United States Patent [19]

Bender et al.

[11] Patent Number: 4,816,577
[45] Date of Patent: Mar. 28, 1989

[54] PROCESS FOR PRODUCING 1-BETA-METHYLCARBAPENEM ANTIBIOTIC INTERMEDIATES

[75] Inventors: Dean R. Bender, Hazlet; Ichiro Shinkai, Westfield; Anthony M. De Marco, Glen Gardner; James A. McCauley, Belle Mead, all of N.J.

[73] Assignee: Merck & Co., Inc., Rahway, N.J.

[21] Appl. No.: 134,589

[22] Filed: Dec. 16, 1987

Related U.S. Application Data

[63] Continuation of Ser. No. 848,530, Apr. 7, 1986, abandoned.

[51] Int. Cl.$^4$ .................. C07B 55/00; C07D 205/08; C07F 7/20; C07F 7/18
[52] U.S. Cl. ...................................................... 540/200
[58] Field of Search .......................................... 540/200

[56] References Cited

PUBLICATIONS

Heterocycles, vol. 21, No. 1, 1984 by David Shih, et al.
Tetrahedron Letters, vol. 26, No. 14, pp. 1739–1742, 1985 by Hideo Hirai, et al.

*Primary Examiner*—Mark L. Berch
*Attorney, Agent, or Firm*—Robert J. North; Hesna J. Pfeiffer

[57] ABSTRACT

A process for isomerizing an alpha methylated azetidinone alkyl ester to the corresponding beta-methyl isomer, which is an intermediate in the synthesis of 1-beta-methylcarbapenem antibacterial agents. The process involves treating the dianion of structure I, being the alpha isomer, with a P-H or S-H containing organic protic acid, organometallic Sn or Pb hydride, metallic cation salt or trialkyl borane, followed by quenching with an OH protic organic acid or mineral acid.

17 Claims, No Drawings

PROCESS FOR PRODUCING 1-BETA-METHYLCARBAPENEM ANTIBIOTIC INTERMEDIATES

This is a continuation of application Ser. No. 848,530, filed Apr. 7, 1986, now abandoned.

BACKGROUND OF THE INVENTION

1. Field of the Invention

This invention relates to a process for producing 1-betamethyl carbapenem antibiotic intermediates involving isomerizing an alphamethylated azetidinone alkyl carboxylic ester under basic conditions.

2. Brief Description of Disclosures in the Art

Since the discovery of thienamycin,

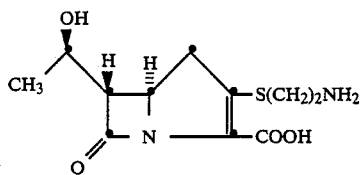

an extremely potent broad spectrum antibiotic, disclosed and claimed in commonly assigned U.S. Pat. No. 3,950,357, a large amount of research activity has been conducted in the medicinal chemistry area for other active analogs not having its associated deficiencies, i.e. chemical instability at high concentration and susceptibility to renal dipeptidase.

In addition to the N-formimidoyl derivative of thienamycin, disclosed and claimed in commonly assigned U.S. Pat. No. 4,194,047, among some of the more promising analogs that have been developed are the 1-betamethyl compounds of the structure, i.e.,

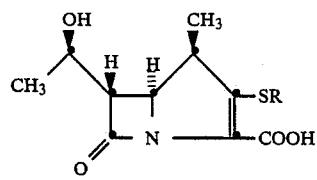

in which the 1-methyl group is in the beta configuration and R is a radical known in the antibiotic art.

Synthesis of the above 1-beta methyl analogs is desired in large quantities for derivatization and pharmacological evaluation and requires a process which is environmentally safe for the introduction of the beta-methyl substituent in a manner designed to yield a high percentage of the beta-methyl intermediate prior to ring closure.

A published procedure by Shih et al. in Heterocycles, Vol. 21, No. 1, pp. 29–40 (1984) describes a process for alkylating the 4-alkyl side chain of certain azetidin-2-ones in the presence of hexamethylphosphoramide (HMPA) as a cosolvent, to produce a mixture of the alpha-and beta-methyl isomers in about a 4:1 molar ratio. Also described is an epimerization process employing HMPA resulting in a 1:1 beta/alpha methyl isomer ratio.

Desirably, a pilot plant or commercial synthesis should achieve higher beta/alpha isomeric molar ratios than this and the use of hexamethylphosphoramide should be avoided due to its known carcinogenicity.

It is therefore an object of this invention to provide a process for producing intermediates useful in making 1-betamethylcarbapenem antibiotics. It is further an object of this invention to provide a process for producing intermediates in high yield having the necessary 1-beta methyl stereochemistry, prior to ring closure to the carbapenem ring system, in which the products contain the beta methyl/alpha methyl isomers in a molar ratio greater than one. These and further objects of the invention will become obvious from the accompanying disclosure as set forth herein.

SUMMARY OF THE INVENTION

It has been found that by treating a dianion of a compound of the structure:

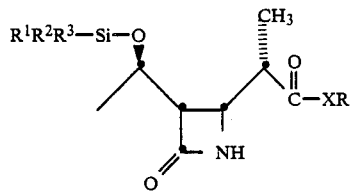

present as is, or in admixture with the beta-methyl diastereomer, with a P-H or S-H organic protic acid, organometallic Sn or Pb hydride, metallic cation salt or a trialkyl borane, followed by quenching with an OH protic organic acid or mineral acid, good yields of the beta methyl isomer are obtained which are useful in the synthesis of 1$\beta$-methyl-carbapenem antibiotics.

In accordance with the invention there is provided an isomerization process comprising the steps of:

(a) contacting the compound:

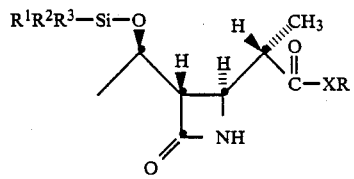

wherein X is —O— or —S—; R is $C_1$–$C_8$ linear or branched alkyl, $C_6$–$C_8$ aryl or a carboxylic acid protecting group; and $R^1$, $R^2$, $R^3$ are selected from $C_1$–$C_8$ linear or branched alkyl, $C_6$–$C_8$ aryl; with at least two equivalents proportionately thereto of an alkali metal amide, in an anhydrous solvent therefor, excluding hexamethylphosphoramide, in an $O_2$-free, moisture-free atmosphere;

(b) contacting the resulting mixture from step (a) with a P-H or S-H organic protic acid, a Sn or Pb organometallic hydride, a metallic cation salt, or tri-$C_1$–$C_6$-alkyl borane;

(c) contacting the resulting mixture from step (b) with an OH organic protic acid or mineral acid, resulting in a mixture of alpha and beta isomers wherein the beta/alpha-methyl isomer ratio is greater than 1.0.

DESCRIPTION OF THE INVENTION AND PREFERRED EMBODIMENTS

The overall subject invention can be easily understood from the following illustrated reaction scheme:

REACTION SCHEME

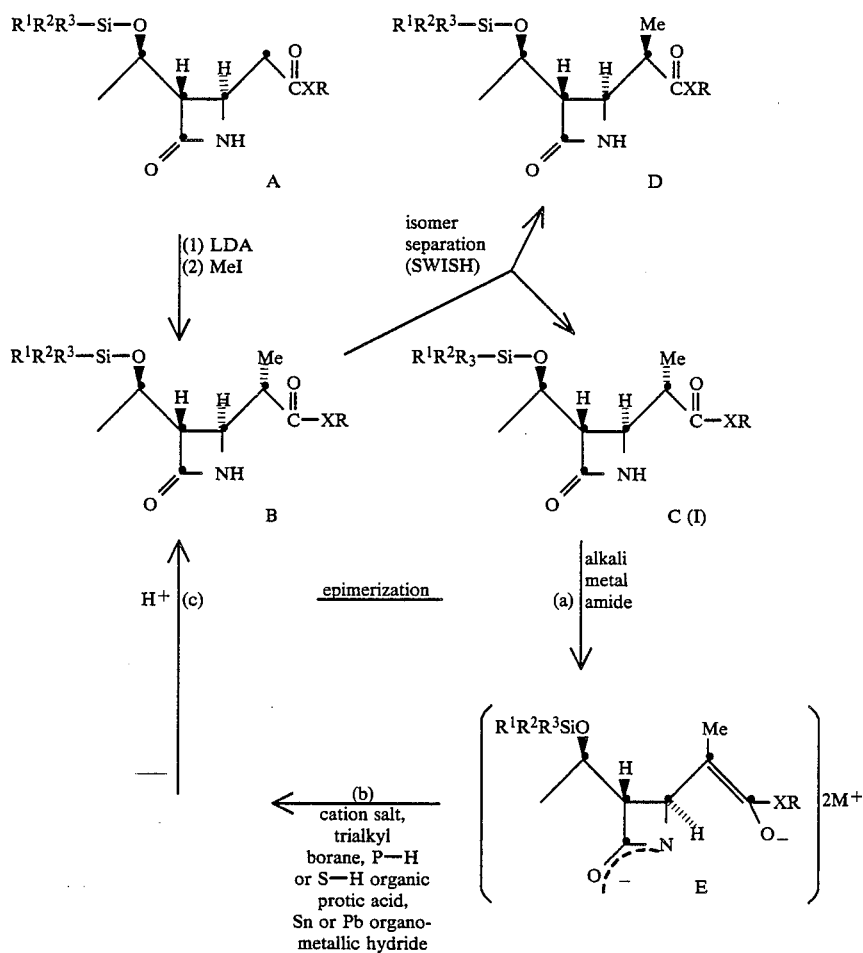

The reaction scheme illustrates the overall process of producing 1-beta-methylcarbapenem intermediates involving the initial step of methylating the azetidinone ester A (wherein X is O) to form the mixed beta and alpha methylated mixture B, as for example, by the method of Shih et al. described hereinabove.

A preferred method for methylating the lithium enolate of the azetidinone ester A is a modification of the above referred to method of Shih et al., hereby incorporated by reference, which involves substantially the same procedure as described but also includes elimination of the use of hexamethylphosphoramide as a cosolvent, followed by warming from the reaction temperature of −78° C. to about −45° C. prior to the quench, to produce a mixture of the alpha- and beta-methyl isomers in about a 1.5:1 molar ratio.

Separation techniques performed on the mixture B, by conventional techniques including high pressure liquid chromatography (HPLC), and the like, and also a new technique, i.e. cyclic selective dissolution (SWISH), described herein, allow the separation of pure 5-beta-methyl azetidinone ester D and the substantially pure alpha methyl isomeric mixture C. Thus, the overall separation and purification process consists of two steps: (a) isomer separation and (b) epimerization. In the reaction scheme, M symbolizes the alkali metal.

The novelty of the subject epimerization process resides in the fact that substantial quantities of the alpha methylated isomer, or of any mixture of both isomers, can be converted readily and very conveniently to the beta methyl isomer under relatively mild and convenient reaction conditions. The overall epimerization process as seen consists generally of three steps involving (a) formation of a dianion by means of an alkali metal amide, followed by step (b) in which the dianion is contacted with a metallic cation containing salt, a P-H or S-H organic protic organic acid, a Sn or Pb organometallic hydride, or a trialkyl borane reagent and in step (c) contacting this resulting mixture with an OH organic protic acid or mineral acid to convert the alpha-methyl isomer substantially in good yield to the beta-methyl isomer. Generally, the reaction results in a mixture of beta- and alpha-methyl isomers which is substantially enriched with respect to the beta isomer, which is then subjected to a separation process to obtain pure beta-methyl isomer.

As is seen above in step (a), the compound C of structure I, preferably being a 5-alpha methylazetidinone 3-substituted 4-alkyl ester or thioester, (wherein the silyl radical is dimethyl-t-butyl silyl) is subjected to the epimerization step. The R radical in the ester group —XR, being —OR or —SR, in Structure I is a linear or branched $C_1$-$C_8$ alkyl, $C_6$-$C_8$ aryl or carboxylic acid protecting group. Representative examples include methyl, ethyl, isopropyl, propyl, butyl, iso-butyl, sec-butyl, benzyl, phenyl, phenethyl, p-nitrophenyl, p-nitrobenzyl, and the like. Preferred is methyl.

The R groups on the silicon protecting group are selected from $C_1$-$C_8$ linear or branched alkyl, or $C_6$-$C_8$ aryl. Representative R groups include methyl, ethyl, propyl, isopropyl, sec-butyl, n-butyl, isobutyl, t-butyl, benzyl, phenyl, phenethyl, p-tolyl, meta-tolyl, 3,5-dimethylphenyl, and the like. A preferred silyl group is dimethyl t-butylsilyl.

The alkali metal amide used in step (a) to form the dianion is an alkali metal di-$C_1$-$C_8$-alkyl amide in which the alkali metal portion may be lithium, sodium, potassium, and the alkyl substituents on the amide may be chosen from methyl, ethyl, propyl, isopropyl, n-butyl, t-butyl, isobutyl, secondary butyl, and cycloalkyl such as cyclohexyl, Preferred is where both groups are the same and particularly preferred being isopropyl and a preferred alkali metal is lithium. A preferred alkali metal amide to form the dianion in step (a) is lithium diisopropylamide. The alkali metal amide may be purchased in commercially available pre-made form or can be prepared in situ from alkyl lithium and amines by known procedures in the art.

The solvent used in step (a) and throughout steps (b) and (c) is generally an anhydrous organic ether in which the ether can be cyclic or acyclic and can contain $C_2$-$C_{10}$ carbon atoms. Representative examples of such solvents include tetrahydrofuran (THF), dioxane, glyme, diglyme, methyl t-butylether, diethyl ether and the like. A preferred ether for use in the process is THF.

The use of a solvent in step (a) is conducted in the absence of hexamethylphosphoramide which in fact is a carcinogenic agent and to be avoided in commercial processes.

The reaction of step (a) is conducted in an oxygen-free, moisture-free atmosphere to avoid contamination or side reactions from occurring with the alkali metal amide and its dianion products and solution.

Generally, the compound of structure I is added in solution to a solution of the amide and in a solvent described above at a temperature at a range of about $-30°$ to about $-50°$ C. with stirring. The reverse mode of addition can also be carried out. Preferred is where the structure I is added to the amide. After the reaction contents have been mixed, to ensure complete dianion formation, they are gently stirred for several hours, e.g. from about 1 to 4 hours. Since the alpha isomer is less reactive as compared to the beta isomer, if a substantial quantity of alpha methyl isomer is present, longer times of stirring may be required to ensure complete dianion formation.

The second step (b) of the process involves reacting the dianio with a P-H or S-H organic protic acid, a Sn or Pb organometallic hydride, a metallic cation salt, or trialkyl borane.

The metallic cation of the cation salt may be singly or multiply charged, and representative examples include sodium, lithium, potassium, calcium, magnesium, zinc, copper, diphenyltin (IV), tin (II), zirconium, iron, titanium, cadmium or cesium. Generally, preferred is a double charged cationic species. A preferred metal cation in the salt is the zinc cation. The cations are utilized as salts for addition purposes in the reaction. Representative examples of anions in the salt include chlorides or other halides, sulfates, sulfonates, acetates, acetylacetonates or similar compounds, hydroxides, alkoxides and the like. A preferred cation for use in the process is zinc, and a preferred salt in the process is zinc chloride.

Trialkyl borane agents may also be reacted with the dianion and are selected from $C_1$-$C_8$ linear or branched alkyl borane compounds. Representative alkyls may be selected from methyl, ethyl, propyl, butyl, isopropyl, isobutyl, secondary butyl, tertiary butyl, cycloalkyl such as cyclohexyl and benzyl. Representative examples include triethylborane, tripropylborane, triisobutylborane and trisec-butylborane. A preferred borane agent which can be utilized in the invention process is triethylborane.

The Sn or Pb organometallic hydrides include trialkyl lead hydrides, triaryltin hydrides and the like. Representative examples include tributyl lead hydride and triphenyltin hydride. Preferred is triphenyltin hydride. See also *Tetrahedron Letters*, Vol. 26, No. 14, pp 1739–1742 (1985) illustrating the use of triphenyltin hydride in the stereoselective kinetic protonation of a chiral azetidinone enolate.

The —SH or —PH containing organic protic acids include diarylphosphines, thiolcarboxylic acids, alkylthiols, arylthiols and the like. Representative examples include thioacetic acid, diphenyl phosphine and thiophenol. Preferred is thioacetic acid.

In step (b), the temperature of the addition of the protic organic acid, metal cation salt or borane reagent to the solution resulting from step (a) is normally conducted in the range of about $-40°$ to $-80°$ C. for a period of 0.3 to 4 hours.

Step (c) consists of contacting the mixture resulting from step (b) with an —OH organic protic acid or mineral acid, thus forming a mixture of the alpha- and beta-methyl isomers.

The —OH containing organic protic acids and mineral acids include protonated oxygen and nitrogen compounds, respectively. Representative examples of said protic acids include alkyl and aryl carboxylic acids, protonated amines and strong mineral acids. Representative protic acids include aqueous ammonium chloride, sulfuric acid, hydrochloric acid, acetic acid, formic acid, and the like. A preferred protic acid in the process is acetic acid.

The addition of the protic acid in step (c) is conducted in the range of $-20°$ to $-100°$ C. and the addition can be made either by adding the acid to the resulting mixture from step (b) or vice versa, preferred is the former mode.

The concentration of Structure I, used in steps (a)–(c) is preferably no more than about 0.3 molar to inhibit precipitation of the enolate salt. Larger concentrations can be used but will result in a two-phase system more difficult to work with.

In the process, proportionately for every mole of starting structure I used:
 (a) 2 or more moles of the alkali metal amide are employed prepared in situ or commercially pre-made;
 (b) if prepared in situ, 2 or more moles of alkyl lithium, eg. butyl lithium, are used to generate the lithium dialkylamide, in which an equal or slightly smaller amount proportionately than the amine is used thus generating at least 2 equivalents of the lithium alkylamide per equivalent of I;
 (c) 1 or moles of cationic salt, trialkyl borane, P-H or S-H protic acid, or Sn/Pb organometallic hydride are used, and preferably two;

(d) at least two moles of protic acid are used in step (c) and an amount at least equal to the amount of butyl lithium used. Sufficient acid should be employed in step (c) to insure neutral workup conditions.

The mixture resulting from the epimerization or isomerization reaction generally results in a beta to alpha isomer mixture in which the beta to alpha isomer ratio is greater than 1.0. Generally, the ratio is in the range of 1.2 and above and can be obtained in the range of 1.4 to 1.6/1.0. When using trialkyl boranes, molar ratios as high as 7.3:1 can be obtained. The resulting mixture containing the substantially enriched mixture containing the beta methyl isomer can be separated into its individual isomers by the common technique of high pressure liquid chromatography (HPLC) both on a laboratory scale and also on a plant scale using conventional apparatus known in the art.

A further method for separating the alpha and beta isomers relies on a "SWISH" method which basically is a multistep selective slurry solvent extraction in which both isomers can be obtained in substantial quantities in substantially pure form. The problem with treating or isolating the respective isomers from the beta/alpha mixture resulting from the epimerization is that the beta isomer, which is the more desired isomer, is the more soluble in the reaction and isolation solvents. Thus, greater efforts are required to isolate the beta methyl isomer from the resulting mixture. Fractional crystallization, unfortunately, favors the least soluble isomer and thus is not applicable in the instant process for large scale preparations for desired purity.

The "SWISH" process involves six steps. Prior to the first step, the beta/alpha-methyl isomer mixture is analyzed by conventional methods, i.e., HPLC, to determine the beta to alpha ratio. If the beta to alpha ratio is below 1.2, as is the case for the methylated products obtained using the methylation methods referred to above, then a solvent such as isopropanol is used in the first slurry extraction step. If in fact the beta to alpha ratio is above 1.2, as is the case for some of the epimerization examples described herein, then a solvent such as toluene is utilized in the first solvent extraction step. Assuming that the beta to alpha ratio is above 1.2, then the first step in the process generally consists of slurrying the mixture with a sufficient amount of the solvent toluene such that the amount of solvent used is sufficient just to dissolve the amount of alpha isomer present and not all of the beta isomer. The slurrying of the mixture in the presence of the solvent is done in conventional enclosed glass, kettle or still type of apparatus with shaking or stirring at temperature within the liquid range of the solvents, generally 0°–45°, preferably 15°–25° at any convenient pressure, preferably about one atmosphere, under a preferably moisture-free atmosphere for a sufficient period of time of about 0.5 to 24 hours to ensure that all of the alpha isomer at this point is dissolved in the mother liquor. The preferred temperature controlling apparatus includes a circulating bath with a cooling/heating unit which allows precise (±1° C.) temperature control. Following the dissolution step, the slurry is then filtered, the undissolved beta is isolated, washed, dried to yield substantially (up to 99.9%) pure beta isomer. The mother liquor containing a mixture of the alpha and beta mixture is evaporated to dryness or to a slurry by stripping off the solvent using conventional techniques. If the mixture is evaporated to a slurry, a second extraction solvent, in this case isopropanol is added and a toluene/isopropanol azeotrope is stripped off until all the toluene is removed. The resulting residue or slurry is then treated with a second extraction solvent, in this case isopropanol. The isopropanol solvent extraction performs essentially the same as the first toluene extraction step in which the isopropanol is used in an amount which is sufficient to dissolve all of the beta-methyl isomer but leaving some of the alpha isomer undissolved. Analogous to the first step, the solid is collected, filtered off, washed and dried to yield substantially pure alpha isomer. The mother liquor is then evaporated as described for the first step, the isopropanol collected for recycle and the residue or slurry mixture is then resubjected to the first toluene step using a smaller amount of solvent in order to then isolate more beta methyl isomer and the entire process repeated again. Conversely, the solvent volumes can be kept the same and make-up solid mixture can be added from the process in a continuous type of manner to then reefect and reinitiate the entire process using the same amounts of solvents and solids as previously. The solvents are chosen on the basis of their solubility ratio parameters with respect to the beta and alpha isomers of the intermediates. The solvent solubility ratio for the beta to alpha isomers for isopropanol is 1.6 to 1 whereas that of toluene is 1.2 to 1. Other solvents that can be used in this extraction process and their respective solubility parameter ratios with respect to the beta and alpha isomers are as follows: cyclohexane (1.16/1), acetonitrile (1.2/1), ethyl acetate/hexane (1.25/1), methyl t-butyl ether (1.4/1), ethanol/water (1.5/1) and n-propanol (1.5/1). The criticality with respect to the process is in the choice of the particular solvents in which the solubility ratios of one solvent to another cannot be equal to 1. There must be a ratio of solubility ratios greater or less than 1 in order for the process to be operable. Any set of two solvents for which the $\alpha/\beta$ solubility ratios in the 2 solvents are not equal may be used. The specific solvents listed above represent examples of types of solvents for which the ratio of solubility ratios is sufficiently different from 1 to provide a practical process.

The applicability of the above-described "SWISH" process is broader is scope than merely being applied to the separation of alpha and beta-methyl azetidinone esters described herein. It is applicable to any diastereomer separation problem when the solubility ratios for two or more solid components in two or more different solvents, or in the same solvent at 2 or more different temperatures, or at 2 or more different pressures, are not equal; and, when the diastereomers crystallize as a eutectic, i.e. as pure substances or as highly enriched solid solutions of essentially constant composition. The process may be applied to a mixture containing a plurality of diastereomers, involving various solvents, and ranges of pressures and temperatures. As expected, application of the process becomes increasingly more complex as the number of diastereomers increases, as more steps are required.

To define a "SWISH" process for 2 diastereomers one first determines the solubilities of the 2 diastereomers in a variety of solvents and over a range of convenient temperatures until one finds a set of 2 conditions (2 solvents at defined pressure and temperature, 1 solvent at a defined pressure and 2 different temperatures, etc.) which provides a useful difference in the solubility ratios of the 2 diastereomers. The survey of solubilities should be carried out on a mixture of the diastereomers in order to take into account any effects they may have on each other. The physical state of the solid phase from the solubility determinations should also be monitored by conventional means (eg, x-ray powder diffraction, differential thermal analysis, microscopy) to determine if the solid is a mixture of pure substances (or a mixture of constant composition, highly enriched solid solutions), or a single solid solution. If the solid phase from a solubility determination is a single solid solution, then these conditions cannot be used in a "SWISH" process. After choosing a satisfactory set of 2 conditions one chooses the appropriate initial solvent and amount as dictated by the amount of mixture to be swished, the diastereomeric ratio of the mixture and the solubility of the diastereomer that is to be completely dissolved.

The following examples are illustrative of the subject invention and should not be construed as being limitations on the scope or spirit thereof.

EXAMPLE 1

Lithium Enolate, HOAc Quench

A solution of n-butyl lithium in hexanes (1.55 M, 10.7 ml) was added to a solution of diisopropylamine (2.43 ml, 17.3 mmol) in tetrahydrofuran (THF, 15 ml) while maintaining the temperature below −20°.To this was added a solution of crude (3S, 4S) −3-[(1R)-1-t-butyldimethylsilyloxyethyl]-4-[(1S)-1-methoxycarbonylethyl]-azetidin-2-one (structure C, where X=0, R=$R^1$=$R^2$=methyl and $R^3$=t-butyl; having the convenient trivial name of "alpha-7") [2.51 g, 81% alpha-7, 1% β-methyl isomer (structure D, where X=0, R=$R^1$=$R^2$=methyl and $R^3$=t-butyl; having the convenient trivial name of "beta-7"), 18% desmethyl at C-5] in THF (7.5 ml) while maintaining the temperature below −32°.The solution was stirred for 3 hours at −40° to −45°,cooled to −78°, then added via cannula to a solution of acetic acid (3.34 ml) in THF (10 ml) while maintaining the quench mixture at less than −40°.Saturated aqueous ammonium chloride (30 ml) and ethyl acetate (20 ml) were added while warming to 20°.The organic layer was separated, the aqueous layer was extracted again with ethyl acetate (20 ml), and the combined organic layers were washed with water (20 ml). The extract (85 ml) was assayed by evaporating 1.0 ml in a 25 ml volumetric flask, diluting to the mark with acetonitrile, then analyzing this sample by HPLC (Altex Ultrasphere-Octyl, 5μ, 25 cm×4.6 mm ID, acetonitrile:water: phosphoric acid (55:45:0.1-v/v), flow rate equal 1.1 ml/min, UV detector at 210 nm, retention times of about 12.7 minutes for beta-7 and 14.0 minutes for alpha-7) against an external standard containing analytically pure sample of each isomer at about 1 mg pure isomer/ml. The assay indicated 0.342 g beta-7 and 1.309 g alpha-7[β/α=21/79 molar ratio, yield (α+β)=80%].

EXAMPLE 2

With HMPA as Cosolvent

The enolate solution was prepared as described for Example 1, except that hexamethylphosphoramide (HMPA, 2.8 ml) was added after the addition of n-butyl lithium, followed by addition of the alpha-7 solution. The resulting solution was aged at −75°/45 minutes, then it was quenched, worked up and assayed as described for example 1 to yield beta-7 (0.715 g) and alpha-7 (0.948 g), β/α=43/57 molar ratio, yield (α+β)=81%.

EXAMPLE 3

Zinc Addition, HOAc Quench

A solution of n-butyllithium in hexanes (1.34 m, 1.2 ml) was added to a solution of diisopropylamine (0.24 ml) in THF (4 ml) while maintaining the temperature below −20°. To this was added a solution of alpha-7 (252 mg, 0.8 mmol) in THF (2 ml) while maintaining the temperature below −40 °. After aging for 3 hours at −40° to −45°, the solution was cooled to −75° and a solution of anhydrous zinc chloride in THF (1.26 M, 1.27 ml) was added. This solution was aged at −75° for 40 minutes, then quenched via cannula into a solution of acetic acid (0.4 ml) in THF (8 ml) while maintaining the quench mixture at less than −65°. After warming the mixture to −20°, water (10 ml) and ethyl acetate (10 ml) were added, and the organic layer was separated and washed with water (10 ml). The extract was assayed as described for Example 1, indicating 96.1 mg beta-7 and 78.0 mg alpha-7 [β/α=55/45 molar ratio, yield (α+β)=70%].

EXAMPLE 4

Magnesium Addition, HOAc Quench

The lithium enolate solution was prepared as described in Example 3 and cooled to −75°. Magnesium bromide (148 mg, 0.8 mmol) was added and the heterogenous mixture was stirred for 1.5 hours at −75° to −55°. The mixture was quenched, worked up and assayed as described for Example 3, yielding beta-7 (86.3 mg) and alpha-7 (114.3 mg), β/α=43/57 molar ratio, yield (α+β)=81%.

EXAMPLE 5

Lithium Enolate, $Ph_3$SnH Addition

The lithium enolate solution was prepared as described in Example 3 and cooled to −75°. A solution of triphenyltin hydride (860 mg, 2.45 mmol) in THF (2 ml) was added while maintaining the temperature below −75°. The solution was aged at −75° for 30 minutes, then a solution of acetic acid (0.4 ml) in THF (1.2 ml) was added while maintaining the temperature below −65°. After warming the mixture to −20°, water (6 ml) and ethyl acetate (6 ml) were added and the separated organic extract was washed with water (6 ml). The extract was assayed as described for Example 1 except that the extract sample was diluted with acetonitrile/water −55/45, and the resulting mixture was filtered before analysis by HPLC: beta-7, 151.3 mg; alpha-7, 60.3 mg [β/α=72/28 molar ratio, yield (α+β)=84%].

EXAMPLE 6

Lithium Enolate, $Et_3B$ Addition, HOAc Quench

The lithium enolate was prepared as described in Example 3 and cooled to −75°. A solution of triethylborane in hexane (1.0 M, 1.6 ml) was added and the solution was aged at −75° for 40 minutes. About half of the solution was quenched via cannula into a solution of acetic acid (0.3 ml) and methanol (0.3 ml) in THF (4 ml) while maintaining the quench temperature less than −65°. The quench mixture was worked up and assayed as described for Example 3. The remainder of the reaction solution was aged an additional 10 minutes at −75°, then the temperature was raised to −45° and the solution was aged for 40 minutes before quenching and working up as described for the first part of the reaction solution.

$\beta/\alpha$ = 76/24 molar ratio for first quench,
= 89/11 for second quench.

Total yield $(\alpha+\beta)$ for both quenches=69%.

EXAMPLE 7
Copper (II) Addition

The lithium enolate solution was prepared as described in Example 3 and cooled to $-75°$. A solution of cupric acetate in THF (0.15 M, 4.2 ml) was added and the solution was aged at $-75°$. for 40 minutes. About half of the solution was quenched, worked up and assayed as described for Example 3. The remainder was aged an additional 10 minutes at $-75°$ then 80 minutes at $-45°$, then quenched, worked up and assayed as described for Example 3. Product from the first quench gave $\beta/\alpha=38/62$ molar ratio; the second quench gave $\beta/\alpha=44/66$. Total yield, $(\alpha+\beta)=47\%$.

EXAMPLE 8
Tin (II) Addition

The lithium enolate solution was prepared as described in Example 3 and cooled to $-75°$. A solution of tin (II) chloride in THF (0.93 M, 1.4 ml) was added and the solution was aged at $-75°$ for 40 minutes. A solution of acetic acid (0.4 ml) in THF (1.2 ml) was added while maintaining the temperature less than $-65°$, then the mixture was warmed to $-20°$, water (6 ml) and ethyl acetate were added, the mixture was filtered through supercell, and the separated organic layer was assayed as described in Example 1 to give $\beta/\alpha=25/75$ molar ratio, yield $(\alpha+\beta)=53\%$.

EXAMPLE 9
Addition of Ph$_2$SnCl$_2$

The lithium enolate solution was prepared as described in Example 3 and cooled to $-75°$. A solution of diphenyltin dichloride (469 mg) in THF (2 ml) was added and the solution was aged at $-75°$ for 1 hour. About half the solution was quenched, worked up and assayed as described for Example 3. The remainder was aged an additional 10 minutes at $-75°$ then 45 minutes at $-45°$, then quenched, worked up and assayed as described for Example 3. The products of both quenches gave $\beta/\alpha=40/60$ molar ratio and a yield $(\alpha+\beta)$ of 25%.

EXAMPLE 10
Epimerization of the Thiomethyl Ester

A solution of n-butyl lithium in hexanes (1.4 M, 1.15 ml) was added to a solution of diisopropylamine (0.24 ml) in THF (4 ml) while maintaining the temperature below $-30°$. To this was added a solution of the thiomethyl ester (structure I where X=S, R=R$^1$=R$^2$=methyl and R$^3$=t-butyl; 265 mg, 0.8 mmol) in THF (1.8 ml) while maintaining the temperature below $-40°$. The solution was stirred for 3 hours at $-40°$ to 45°, then it was cooled to $-75°$. A solution of anhydrous zinc chloride in THF (1.26M, 1.27 ml) was added, and the solution was aged at $-75°$ for 45 minutes. A solution of acetic acid (0.4 ml) in THF (1.2 ml) was then added while maintaining the temperature less than $-65°$. After warming the resulting mixture to $-20°$, the reaction was worked up and assayed as described for example 3, indicating 49 mg of the $\beta$-methyl isomer and 105 mg of the $\alpha$-methyl isomer [$\beta/\alpha=32/68$ molar ratio, yield $(\alpha+\beta)=58\%$].

EXAMPLE 11
Isolation of a Solid Mixture of Alpha-7 and Beta-7 from an Epimerization Extract An extract (233 L) containing beta-7 (1.14 kg) and alpha-7 (0.78 kg) was concentrated in vacuo to a mixture (about 40 L) which had separated into organic and aqueous phases containing acetic acid from the epimerization quench. Solid sodium bicarbonate (1 lb) was added to the agitated phases, and the separated organic phase was washed with saturated sodium bicarbonate solution (2×4 L), water (4 L) and brine (4 L), then evaporated in vacuo to a residue which was flushed with heptane (3×2 L). the crude residue (4.0 kg) was mixed with heptane (4 L) and heated to 70° in order to dissolve the solids. The batch was cooled over several hours to about 10° and aged at 10° for 10–12 hours. The resulting solid was collected by filtration, washed with cold (0°-5°) hexanes (4×1 L), and air dried at 45°-50° to yield a white solid (1.43 kg) having a wt % purity $(\alpha+\beta)$ of 86% and a molar isomer composition ratio of $\beta/\alpha=60/40$. (A dimethylated contaminant is the major cause of the low wt % purity.)

A second crop of material was obtained in similar fashion: 320 g, wt % purity $(\alpha+\beta)=76\%$, $\beta/\alpha=52/48$.

EXAMPLE 12
The "Cyclic SWISH" Procedure for Separating the Alpha- and Beta-methyl Isomers

Isolation of Alpha-7 From Solid Mixture

A 33-liter resin kettle was equipped with a mechanical stirrer, thermometer and a coiled tube connected to a controlled temperature circulating bath. A mixture of alpha-7 and beta-7 (gross weight =9.21 kg, alpha-7=6.04 kg, beta-7=3.02 kg) was charged to the vessel along with isopropyl alcohol (IPA, 14.35 l). The volume of IPA was determined by multiplying the amount of beta-7 by its solubility in IPA at 20° (4.75 ml solvent/g beta-7). The resulting slurry was heated at 40° for 1 hour, cooled over 2-3 hours to 20°, then aged at 20° for 12-14 hours. The solid was collected by filtration and the cake was washed with IPA/H2O (3/2, v/v, 3×1.5 l), suction dried for 1 hour, then dried in an air oven at 45°-50°; yielding 4,317 g solid having wt% purity $(\alpha+\beta)$ of 100% and a molar isomer composition ratio of $\alpha/\beta=96.4$. Solids and filtrates were assayed by HPLC as described in Example 1.

Isolation of Beta-7 From Filtrate of Previous Isolation

Mother liquor and washes from the previous isolation were evaporated on a Buchi rotovap in a tared, 20 liter round bottom flask to a thick slurry, which was flushed with toluene (5×2 liter). The weight of residual toluene was determined by subtracting tare weight and total solids (2.666 kg beta-7, 1.683 kg alpha-7), and the total volume of toluene to be used (10.43 liters) was determined by multiplying the amount of alpha-7 by its solubility in toluene at 25° (6.20 ml solvent/g alpha-7). The toluene slurry was transferred to the resin kettle, and the remaining toluene to be added (10.43 liters minus residual toluene in slurry) was added as a rinse while keeping the batch temperature less then 25°. The batch was aged at 25° for 12–14 hours. The solid was collected by filtration, washed with a hexane/toluene mixture (80/20, v/v, 3×300 ml), suction dried for 1 hour, then air dried at 40°–45° to yield 587 g solid having a wt % purity (β) of 99+%.

Isolation of alpha-7 From Filtrate of Previous Isolation

Mother liquor and washes from the previous isolation were evaporated as previously described to a thick slurry, which was flushed with IPA (5×2 liter). The weight of residual solvent (IPA) was determined as previously described (beta-7=1.91 kg; alpha-7=1.62 kg), and the total volume of IPA to be used (9.07 liter) was determined as described in the first example by multiplying the amount of beta-7 by its solubility in IPA at 20° (4.75 ml solvent/g beta-7). The IPA slurry was transferred to the resin kettle, and the remaining IPA to be added (9.07 liter minus residual IPA in slurry) was added as a rinse while keeping the batch temperature less than 20°. To this slurry was added another portion of solid mixed isomers (2.775 kg alpha-7, 1.387 kg beta-7), which required the addition of more IPA (6.59 liter) to keep the additional beta-7 in solution. The slurry was heated at 35° for 2 hours, cooled to 20° over 2–3 hours, then aged at 20° for 12–14 hours. The solid was collected by filtration and the cake was washed with IPA/H$_2$O (3/2, v/v, 3×1 liter), suction dried for 1 hour, then dried in an air oven at 40°–45°, yielding 2,472 g solid having a wt % purity (α+β) of 100% and a molar isomer composition ratio of α/β=94/6. The filtrate and washes were treated as described in the second example to yield more pure beta-7.

EXAMPLE 13

Methylation without Hexamethyl Phosphoramide as Cosolvent

A solution of n-butyl lithium in hexane (1.38 M, 5.14 ml) was added to a solution of diisopropylamine (1.03 ml, 7.35 mmol) in tetrahydrofuran (THF, 5 ml) while maintaining the temperature below −30°. After cooling this solution to 78°, a solution of (3S, 4R)-3-[(1R)-1-t-butyldimethylsilyloxtyethyl]-4-methoxycarbonylmethylazetidin-2-one (1.07 g, 3.55 mmol) was added while maintaining the temperature below −70°. The solution was stirred for 45 minutes at −75° C., then methyl iodide (0.5 ml, 8.0 mmol) was rapidly added while maintaining the temperature below −70° C. The resulting mixture was stirred at −70° to −75° C. for 1 hour then at −50° to −55° C. for 1 hour. Acetic acid (1.0 ml) was added while maintaining the temperature below −50° C., then the batch was warmed to −20° C. and water (10 ml) followed by ethyl acetate (10 ml) were added. The separated organic layer was washed with water (10 ml) to yield an extract (31.7 ml)) which was assayed as described for Example 1 to yield beta-7 (323 mg) and alpha-7 (453 mg), β/α=42/58 molar ratio, yield (α+β)=73%.

What is claimed is:
1. An isomerization process comprising the steps of:
(a) contacting the compound:

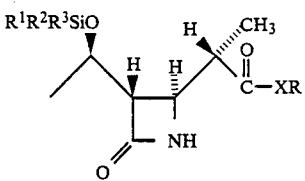

where X is —O— or —S—; R is a carboxylic acid protecting group; and R$^1$, R$^2$, R$^3$ are selected from C$_1$–C$_8$ linear or branched alkyl, C$_6$–C$_8$ aryl; with at least two equivalents proportionately thereto of an alkali metal amide in an anhydrous solvent therefore, excluding hexamethylphosphoramide, in an oxygen-free, moisture-free atmosphere;
(b) contacting the resulting mixture from step (a) with a P-H or S-H organic protic acid, a Sn or Pb organometallic hydride, a metallic cation salt, or tri-C$_1$-C$_6$ alkylborane;
(c) contacting the resulting mixture from step (b) with an OH organic protic acid, or mineral acid, resulting in a mixture of alpha and beta isomers wherein the beta/alpha-methyl isomer ratio is greater than 21/79.
2. The process of claim 1 wherein the temperature range for step (a) is in the range of about −30° to −50° C.
3. The process of claim 1 wherein the temperature range for step (b) is about −40° to −80° C.
4. The process of claim 1 wherein the temperature range for step (c) is −20° to −100° C.
5. The process of claim 1 wherein said alkali metal of said alkali metal amide is lithium.
6. The process of claim 5 wherein said alkali metal amide is lithium diisopropylamide.
7. The process of claim 1 wherein said solvent is a C$_2$–C$_{10}$ -cyclic or acyclic ether.
8. The process of claim 7 wherein said solvent is tetrahydrofuran.
9. The process of claim 1 wherein step (b) said metallic cation in said salt is selected from the cations zinc, copper, diphenyltin, calcium, magnesium, tin, cadmium; the trialkylborane is selected from triethylborane, tripropylborane triisobutylborane or tri sec-butylborane; the protic acid is selected from thioacetic, or thiophenol; and the organometallic hydride is selected from tributyllead hydride or triphenylstannic hydride..
10. The process of claim 1 wherein said protic organic acid in step (c) is acetic acid.
11. The process of claim 1 wherein said beta/alpha-methyl isomer ratio is at least 1.2 to 1.
12. The process of claim 1 wherein the compound of structure I is:

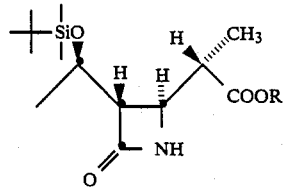

13. The process of claim 1 further comprising the step of (d) separating the beta- and alpha-methyl isomers.

14. The process of claim 13 further comprising separating the alpha-and beta-methyl isomers comprising the steps of (a), treating the beta-alpha mixture with a first solvent to completely dissolve on isomer, (b) performing a first filtration, (c) evaporating off said first solvent and (d) treating the obtained residue with a second solvent to completely dissolve the other isomer, (e) performing a second filtration, (f) evaporating off said second solvent, (g) repeating said steps (a)-(f), wherein the first filtration yields substantially pure one isomer, the second filtration yields substantially pure other isomer, and wherein each solvent having a beta-alpha isomer solubility ratio, wherein the ratio of the solubility ratios is not equal to 1.0.

15. A process for isomerizing the compound:

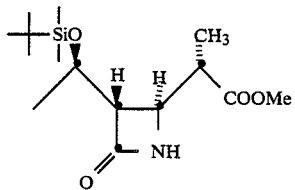

comprising the steps of:
(a) contacting said compound with lithium diisopropylamide in THF under a moisture and oxygen-free atmosphere in the temperature range of −30 to −50° C.;
(b) contacting the resulting mixture from step (a) with a zinc salt in the temperature range of −40° to −80° C.;
(c) contacting the mixture from step (c) with acetic acid in the temperature range of −40° to −100° C.; and
(d) separating the alpha and beta-methyl isomers by the "Swish cycle" method.

16. A process for isomerizing the compound:

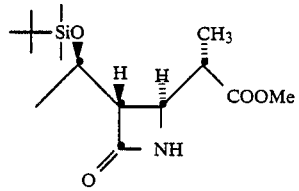

comprising the steps of:
(a) contacting said compound with lithium diisopropylamide in THF under a moisture and oxygen-free atmosphere in the temperature range of −30° to −50°°C.;
(b) contacting the resulting mixture from step (a) with triethylborane in the temperature range of −40° to −80° C.;
(c) contacting the mixture from step (c) with acetic acid in the temperature range of −40° to −100° C.; and
(d) separating the alpha and beta-methyl isomers by the "Swish cycle" method.

17. The process of claim 1 wherein R is $C_1$–$C_8$ linear or branched alkyl or $C_6$–$C_8$ aryl.

* * * * *